US005710041A

United States Patent [19]

Moorman et al.

[11] Patent Number: 5,710,041

[45] Date of Patent: Jan. 20, 1998

[54] IN SITU RECONSTITUTABLE LYOPHYLIZED BACTERIA AMPOULE PACKAGE

[75] Inventors: Dale T. Moorman, Prairie Village, Kans.; Mary Ann Silvius, Kansas City, Mo.

[73] Assignee: Remel L.P., Lenexa, Kans.

[21] Appl. No.: 657,159

[22] Filed: Jun. 3, 1996

[51] Int. Cl.[6] .................................................... C12M 1/24

[52] U.S. Cl. .................................... 435/287.6; 435/288.2; 435/304.2; 435/307.1; 435/810; 604/87; 604/90; 222/94; 222/145.5

[58] Field of Search .......................... 435/30, 260, 283.1, 435/287.6, 288.2, 304.2, 307.1, 309.1, 810; 222/145.5, 420, 540, 541.3, 94; 604/82, 87, 88, 89, 90, 92; 436/808, 810

[56] References Cited

U.S. PATENT DOCUMENTS

| | | | |
|---|---|---|---|
| 2,619,448 | 11/1952 | Larsen | 435/260 |
| 3,360,440 | 12/1967 | Haab et al. | 435/287.6 |
| 4,950,237 | 8/1990 | Henault et al. | 604/82 |
| 4,978,504 | 12/1990 | Nason | 435/287.6 |
| 5,035,348 | 7/1991 | Seifert . | |
| 5,091,316 | 2/1992 | Monthony et al. . | |
| 5,100,028 | 3/1992 | Seifert . | |
| 5,155,039 | 10/1992 | Chrisope et al. | 435/307.1 |
| 5,256,537 | 10/1993 | Phillips et al. | 435/287.6 |
| 5,279,964 | 1/1994 | Chrisope . | |
| 5,362,654 | 11/1994 | Pouletty | 436/518 |
| 5,474,209 | 12/1995 | Vallet Mas et al. | 222/83 |

OTHER PUBLICATIONS

"Instructive Insert for CULTI–LOOPS"; Chrisope Technologies, Inc., Lake Charles, LA (No Date Provided).

*Primary Examiner*—William H. Beisner
*Attorney, Agent, or Firm*—Hovey, Williams, Timmons & Collins

[57] ABSTRACT

An in situ reconstitutable biological ampoule package is provided which includes an open-ended container having non-frangible, deformable wall structure for receiving a quantity of lyophylized bacteria. An ampoule within the container stores a quantity of a liquid medium for reconstituting the bacterial product. Application of pressure to the ampoule by squeezing of the container effects deformation of the side wall of the ampoule thereby releasing the liquid for reconstitution of the biological product. The ampoule may be either of glass which breaks when subjected to pressure, or of synthetic resin material which collapses when squeezed, thereby causing the stored liquid to be ejected from the ampoule through an aperture in the side wall thereof. A dropper cap closing the open end of the container allows the user to apply the reconstituted bacterial product in a drop-wise fashion to a target medium.

7 Claims, 2 Drawing Sheets

52 50 48 44 28 46 32 38 20 36 22 24 42 36a 36b 40 30 26

120
122
124
126
128
130
132
144
148
154
156
158
160

IN SITU RECONSTITUTABLE LYOPHYLIZED BACTERIA AMPOULE PACKAGE

BACKGROUND OF THE INVENTION

1. Field of the Invention

This invention relates to a lyophylized biological agent package permitting the user to reconstitute the dry agent and then apply the liquified material drop-wise to a selected target medium. A more uniform and efficient transfer of the bacterial agent from the package to the point of use is thereby assured.

2. Description of the Prior Art

A wide variety of biological laboratory procedures require application of bacterial agents or the like to a suitable growth medium. In the past, a number of different delivery systems have been proposed and placed in commercial practice, but each has disadvantages and drawbacks in delivery of the biological agent to the growth medium.

For example, in one prior unit, an elongated plastic sleeve heat-sealed at one end thereof houses a glass ampoule which contains a rehydrating fluid. A cotton pladget rests against the glass ampoule to retain the latter in position at one end of the plastic sleeve. A swab impregnated with the bacterial agent and provided with an elongated stem is carried within the sleeve in disposition whereby the swab rests against the pladget. A cap over the open end of the plastic sleeve may be removed to provide access to the outer end of the swab stem. A plastic cylinder over the sleeve may be shifted into disposition surrounding the glass ampoule. In use, the laboratory technician adjusts the position of the sleeve so that it overlies the glass ampoule. Sufficient pressure is applied to the cylinder to compress the plastic sleeve and crush the glass ampoule. Liquid stored in the ampoule is thereby released which seeps through the pladget and is soaked up by the cotton swab. Upon removal of the swab from its protective sleeve, the swab may be used to inoculate plates containing a growth medium such as agar agar.

This bacteria delivery system is exemplified by the Quali Swab of Becton, Dickenson & Company. This delivery unit has inherent deficiencies because of the potential for injury to the user thus exposing the technician to a live bacteria. In addition, there is a limitation on the number of inoculations of the growth medium that may be accomplished. Another type of swab transport and delivery device is illustrated and described in B&D U.S. Pat. No. 5,091,316.

In Microbiologics' Quick Stick, a plastic sleeve houses an elongated swab stick which is positioned between a glass ampoule containing the reconstitution fluid and a pellet of the lyophylized bacteria. A porous cotton support for the outer end of the swab stick is located in proximal relationship to the glass ampoule; the cotton swab is positioned adjacent the bacteria pellet. Upon fracture of the glass ampoule by compression pressure, the released liquid flows through the cotton support and eventually reaches the organism pellet to effect reconstitution of the bacteria. Deficiencies of this delivery system include the possibility of a puncture wound thus exposing the user to live bacteria, and the fact that fluid can flow out of the tube assembly if it is rested on the laboratory bench, creating a messy environment and possible contamination of the test area.

The Culti-Loop of Chrisope Technologies, as disclosed in U.S. Pat. No. 5,279,964 relies upon the use of a loop supporting the lyophylized microorganism and provided with an elongated handle to facilitate manipulation of the loop. In this instance, users must provide their own rehydrating liquid, dip the loop into the liquid, and then apply the loop to the growth medium. Again, there is a limitation on the number of inoculations that may be accomplished using a single loop and there are personnel inoculation dangers associated with handling of the live bacteria with apparatus of this type. Furthermore, it is difficult to deposit the same quantity of bacteria on multiple growth medium sites from a single loop.

Another long-practiced culture procedure involves reconstitution of freeze-dried pellets of the organism to be tested in a glass vial, which are conventionally furnished in the form of 10 pellets per vial. Tweezers are used to remove a selected number of the pellets from the vial and to place the pellet or pellets in a test tube. Rehydrating liquid is added to the test tube and the bacterial agent allowed to dissolve. A swab or loop is then used to inoculate the growth media. This procedure not only exposes the laboratory technician to the live virus, but also as indicated previously, makes it difficult for the user to accurately transfer the same number of bacteria cells to each selected site on the media.

U.S. Pat. No. 5,100,028 of Institute Guilfoyle discloses a fluid dispenser made up of a flexible fluid-containing vessel which seals a top wall of the vessel to a bottom wall and is shaped to concentrate forces applied to the sides of the dispenser on the liquid contained therein so as to open the seal and allow fluid to be ejected from the container through an opening in the normally sealed part of the dispenser. The unit is said to useful for dispensing food items, various cosmetic products and medicaments in the nature of vitamins or ointments.

SUMMARY OF THE INVENTION

The present invention provides an in situ reconstitutable biological ampoule package which allows the technician to apply essentially the same volume of the reconstituted biological agent to multiple growth medium sites from a single package without significant live bacteria inoculation dangers to the user. This is accomplished at a reasonable cost and in a commercially reproducible manner.

The package includes a cylindrical container which is closed at one end and that has a non-frangible, deformable side wall. The container receives a pellet of the lyophylized bacterial agent and also houses an ampoule which stores the liquid medium for reconstituting the bacteria.

In one form of the invention, the ampoule is glass and a protective cover is provided around the container to prevent injury to the user when pressure is applied to the side wall of the container sufficient to break the glass. In another embodiment of the invention, the ampoule is of synthetic resin material crimped and bonded at one end to present an integral substantially V-shaped end closure. The side wall of the ampoule in the crimped area has an aperture therein normally closed by an opposed part of such crimped section of the ampoule. When pressure is applied to the ampoule by compression of the surrounding part of the container, such pressure on the liquid stored in the ampoule exerts a force on the crimped part thereof thus separating the bonded parts of the side wall of the ampoule to an extent that liquid may flow through the side wall aperture to reconstitute the lyophylized bacteria pellet.

A dropper cap over the open end of the container allows the user to apply drops of the reconstituted bacterial agent to selected sites of a growth medium. In view of the fact that the drops are essentially of the same volume, the same amount of the bacterial agent may be applied to the selected individual sites on the plate.

DETAILED DESCRIPTION OF THE PREFERRED EMBODIMENTS

Figures 1, 2, 3, 4, 5:
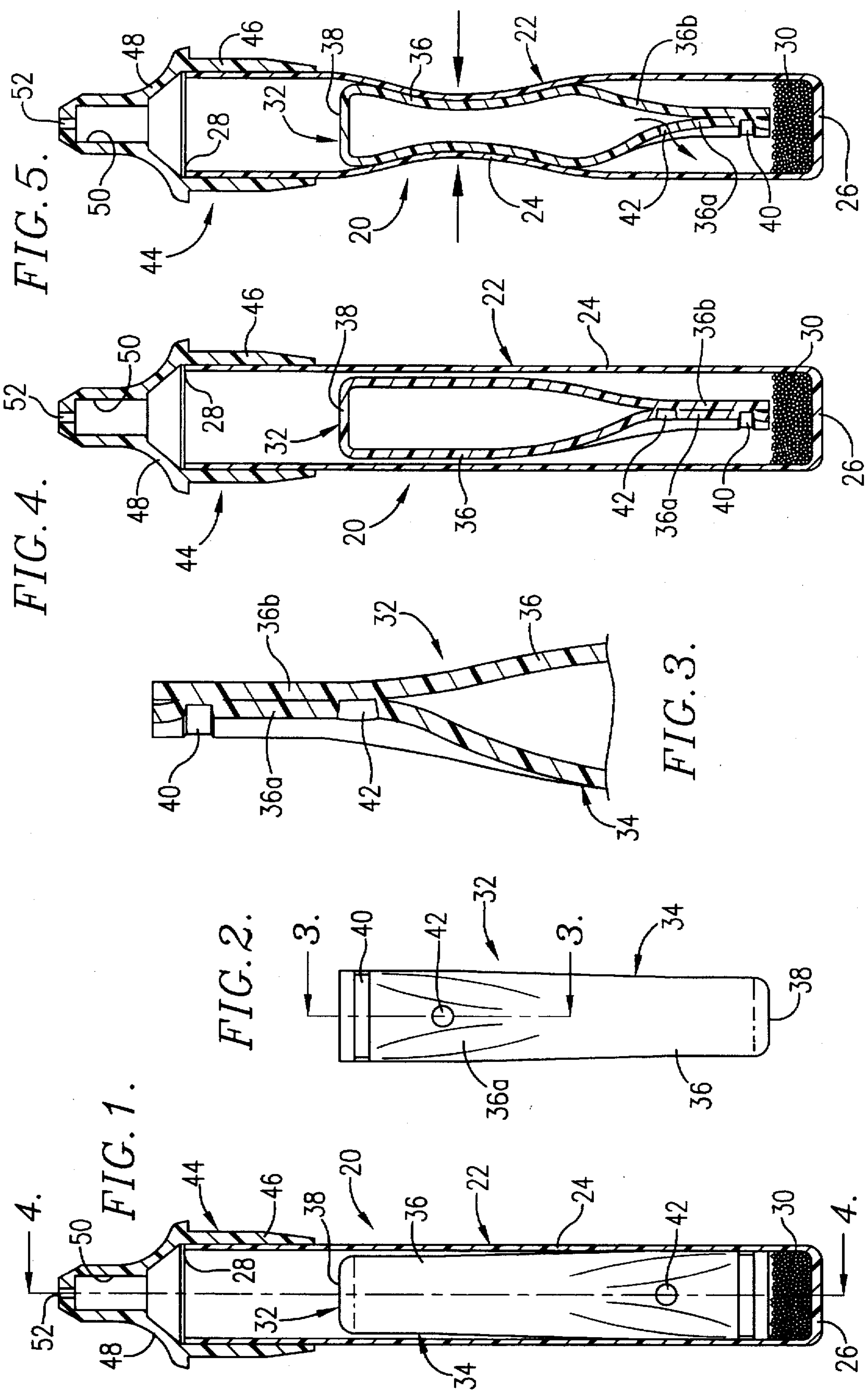
FIG. 1 is a vertical cross-sectional view of an ampoule package constructed in accordance with the preferred embodiment of the invention and illustrating the cylindrical main container, the pellet of lyophylized bacterial agent received within the container, the reconstituting liquid ampoule of synthetic resin material and normally located adjacent the pellet, and a dropper cap normally closing the main container.
FIG. 2 is a elevational view of the ampoule which contains the reconstituting liquid for the lyophylized bacteria pellet.
FIG. 3 is an enlarged fragmentary cross-sectional view taken substantially along the line 3—3 of FIG. 2.
FIG. 4 is a vertical cross-sectional view similar to FIG. 1 but also showing the ampoule in cross-section.
FIG. 5 is a vertical cross-sectional view taken along the same line as the cross-sectional view of FIG. 4 but illustrating in this instance the manner in which liquid is dispensed from the ampoule into the interior of the main container when the latter is squeezed in directions as indicated by the opposed arrows of the Figure.

An in situ reconstitutable lyophylized biological ampoule package constructed in accordance with the preferred embodiment of the present invention is broadly designated by the numeral 20 and depicted in FIGS. 1–5 of the drawings. Package 20 includes a main container 22 preferably formed of a synthetic resin material such as polyethylene in order to render the unit at least semi-transparent. Container 22 has a cylindrical side wall 24 which is integral with a bottom wall 26 which serves to close one end of the cylinder defined by container 22. As is apparent from FIG. 1, container 22 has a longitudinal axis of significantly greater length than the cross-sectional diameter of the cylinder. The end 28 of main container 22 is normally fully opened as shown in FIGS. 1, 4 and 5.

It is to be understood in this respect that main container 22 is constructed of the dimensions, wall thickness and synthetic resin material well known to those skilled in the art such that it is substantially self-sustaining, but side wall 22 may be compressed by applying finger pressure thereto, normally between the user's thumb and forefinger. The components of package 20 as illustrated in FIG. 1 for example are substantially to scale.

A normally dry, solid pellet 30 of a biological agent is received within main container 22 and generally rests on the inner surface of bottom wall 26. Pellet 30 may for example comprise about 0.2 ml on a volume basis of lyophylized bacteria. Exemplary organisms in this respect include bacteria within the genus *acinetobacter, aeromonas, alcaligenes, bacillus, bacteroides, bordetella, candida, citrobacter, celostridium, corynebacterium, cryptococcus, enterobacter, enterococcus, escherichia, flavobacterium, fusobacterium, gardnerella, haemophilus, klebsiella, micrococcus, moraxella, neisseria, oligella, peptostreptococcus, proteus, pseudomonas, salmonella, serratia, shewanella, shigella, staphylococcus, streptococcus, vibrio, xanthomonas*, and *yersinia*. Two hundred or more species of lyophylized bacteria samples are typically available from a number of commercial suppliers, including the assignee hereof. Other bacterial organisms may also be dispensed using package 20 in a manner as described hereinafter, Typically the organism is freeze-dried in association with carrier material including skim milk, dextrose, ascorbic acid and gelatin to yield a gel which is then flash-frozen.

Ampoule 32 is also preferably constructed of synthetic resin material such as polyethylene and comprises a body 34 having a cylindrical side wall 36 which is integrally connected to a bottom wall 38. Although not depicted in the drawings, it is to be understood that the ampoule contains a quantity of a reconstituting fluid, which in the case of lyophylized bacteria, may consist of either sterile water or tryptic soy broth "TSB". The amount of liquid contained in ampoule 32 is a function of the size of the pellet 30 and the desired degree of reconstitution desired for that particular pellet. Again, as will be understood by those skilled in this art, the side wall 36 of the body 34 making up ampoule 32 is of a thickness and the dimensions of the ampoule are such that the ampoule is essentially self-sustaining, but may be compressed as depicted in FIG. 5 using finger-applied pressure.

The extremity of cylindrical side wall 36 remote from bottom wall 38 is crimped and heat-sealed after incorporation of the liquid reconstitution medium therein as is best evident from FIG. 3. It can be seen from FIGS. 3, 4 and 5, that two opposed segments **36*a* and 36*b* of side wall 36 are crimped and forced together and thereafter heat-sealed as at area 40 to present a liquid-tight seal. However, segment 36*a* for example is provided with an aperture 42 that is formed in the side all 36 at the time of injection molding of the ampoule body 34. However, during crimping and heat-sealing of the segments 36*a* and 36*b* of side wall 36, aperture 42 is normally closed by the opposed wall segment 36*b* of side wall 36**.

It is to be seen from FIGS. 1, 4 and 5 that the filled ampoule 32 is positioned within container 22 in disposition such that the cramped and heats-sealed end thereof opposed to end wall 38, is in facing, proximal relationship to the lyophylized pellet 30. This causes the aperture 42 in segment **36*a* of side all 36 to be located adjacent the pellet 30**.

A dropper cap 44 is placed over the open end 28 of container 22 after insertion of pellet 30 and the filled ampoule 32 into the container. Cap 44 has a cylindrical body portion 46 of dimensions to complementally fit over the open end 28 of cylindrical side wall 24 in frictional engagement therewith. The nozzle portion 48 of cap 44 is integral with body portion 46 and is provided with a main passage 50 which communicates with the orifice 52 at the outer extremity of nozzle 48.

As alluded to above, the lyophylized bacteria pellet is inserted in container 22, the ampoule filled with reconstituting liquid is placed in container 22 with the crimped portion thereof facing the pellet 30, and dropper cap 44 positioned on the open end 28 of container 22 as shown in FIGS. 1, 4 and 5. The package 20 thus presented is in condition for being distributed to bacteriological laboratories for use.

A laboratory technician may use the package 20 to inoculate a selected growth medium in a petri dish or other appropriate container by first squeezing the side wall 24 between thumb and forefinger in the direction of the arrows as depicted in FIG. 5 to thereby apply pressure to the side wall 36 of ampoule body 34. The opposed forces against the side wall 36 of ampoule 32 cause the liquid contained in the latter to be displaced in a direction toward the crimped and sealed end of the ampoule body 34. Fluid pressure against the crimped end of ampoule 32 exerts forces tending to separate the end segments **36*a* and 36*b*, thereby partially tearing apart the heat-seal bond between such segments and bringing the aperture 42 into fluid communication with the interior of the ampoule 32. Opening of the aperture 42 allows the liquid stored within ampoule 32 to flow outwardly through such aperture and to cause a stream of the liquid under pressure to be directed toward the lyophylized bacteria pellet 30. This stream of liquid ejected under pressure from the ampoule 32 not only assists in breakup of the pellet, but also assures rapid reconstitution of the biological agent 30**.

After reconstitution of the biological agent, the laboratory technician may apply the biological material to a suitable growth medium by placing the nozzle 44 directly above the area of such medium where the bacterial agent is to be deposited, and squeeze the main container 20 only to an extent to cause a single drop of the liquified bacterial agent to be emitted from orifice 52 of nozzle 44 and to fall therefrom onto the growth medium. The technician thereby has total control over the application of the biological agent to the growth medium, and the amount of liquid applied to each area of the growth medium is essentially the same, because all droplets are of the same size. Furthermore, the need to use tweezers to transfer the lyophylized bacteria pellet from a supply vial to a dissolution tube is totally eliminated, and the technician is assured that the right type and amount of the reconstitution liquid is supplied in all instances.

In the alternate embodiment of the invention shown in FIGS. 6–10, inclusive, the package 120 is provided with a main container 122 which is identical in construction, material and size to main container 22 previously described. Similarly, the main container 122 receives a dry pellet 130 containing the test biological agent, as for example lyophylized bacteria in a carrier therefor. The pellet 130 rests on the bottom wall 126 which is integrally joined to the side wall 124 of main container 122.

Figures 6, 7, 8, 9, 10:
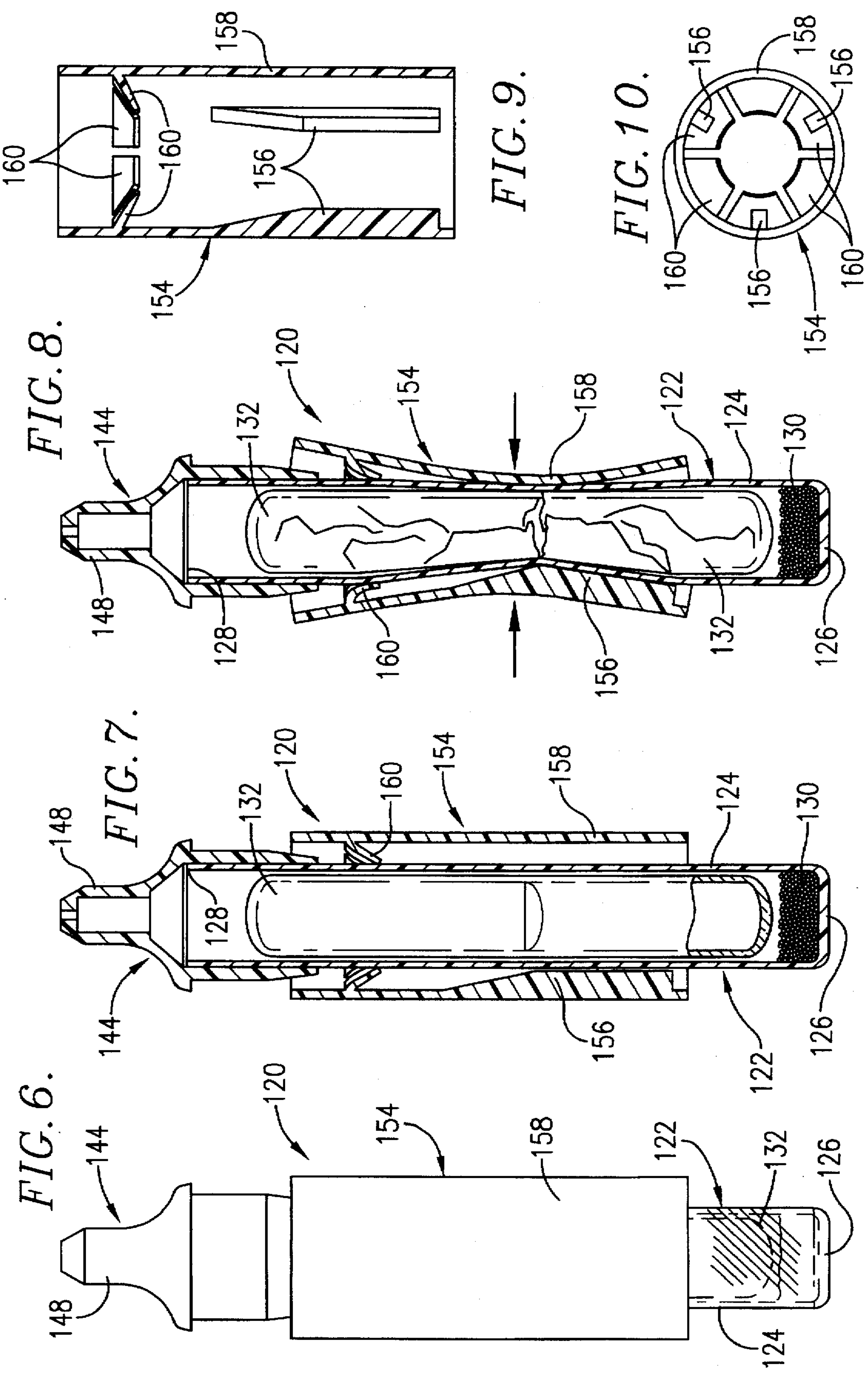
FIG. 6 is a side elevational view of an alternate embodiment of the invention wherein the ampoule is of glass, and a cylindrical protective cover member is provided over the main container.
FIG. 7 is a vertical cross-sectional view of the package as shown in FIG. 6.
FIG. 8 is a vertical cross-sectional view similar to FIG. 7 but illustrating the manner in which the glass ampoule is fractured by application of compressive forces on the cover member and thereby the main container in directions indicated by the arrows on the Figure.
FIG. 9 is a cross-sectional view of the cover member for the main container.
FIG. 10 is a plan view of the cover member illustrated in FIG. 9.

In this instance though, the reconstituting liquid is contained in a glass ampoule vial 132 that is sealed at both ends. A protective cover 154 is slidably telescoped over the side wall 124 of main container 122. As can best be seen from FIGS. 9 and 10, the cylindrical cover 154 has a series of inwardly directed radial ribs 156 extending longitudinally of the cylindrical sleeve portion 158 of cover 154 and located approximately 120° from one another. The innermost longitudinally extending surfaces of ribs 156 lie in an imaginary cylinder which is only slightly greater than the external diameter of side wall 124 of main container 122. A number of integral, radially extending tabs 160 project inwardly from the inner face of cylindrical sleeve portion 158 toward the center of the cover member. The tabs 160 are of a length such that when protective cover 154 is slipped over the main container 122, the tabs 160 deflect as shown in FIGS. 7 and 8 and frictionally engage the outer face of side wall 124 of container 122 to frictionally retain the cover member 154 on the main container 122.

The use of package 120 to inoculate a growth medium surface with biological agents such as bacteria cells, is similar to that described with respect to package 20. To that end, a lyophylized pellet 130 containing a desired biological agent is placed in the main container 122 so that it rests on bottom wall 126 thereof, whereupon a pre-prepared ampoule 132 containing a requisite amount of reconstitution liquid, is introduced into the interior of the main container 122. A dropper cap 144 identical in construction to dropper cap 44 shown in FIGS. 1, 4 and 5, is placed over the open end 128 of main container 122. In like manner, the protective cover 154 is telescoped over the free end of main container 122.

The use of package 120 is identical to that previously described with respect to package 20, except for fracturing of the glass ampoule 132. Breaking of the glass ampoule 132 is accomplished by application of pressure to protective cover 154 using the thumb and forefinger as indicated above, sufficient to deform opposed parts of the side wall 124 of main container 122 inwardly thereby transferring such pressure to the glass ampoule and causing it to fracture, thus releasing the reconstitution liquid within such ampoule. The pressure against protective cover 154 is applied to the outer opposed surface portions of side wall 124 through the medium of ribs 156. Protective cover 154 thus serves the function of transferring pressure from the protective cover 154 to the side wall 124 of main container 122 as lines of contact which focus the pressure. Furthermore, spacing of the cylindrical portion 158 of protective cover 154 away from the outer surface of side wall 124 precludes glass shards produced upon fracture of the glass ampoule 132 from cutting through the wall 124 of main container 122 and causing injury to the fingers of the laboratory technician.

Although not shown, it is to be appreciated that a removable cap may be provided over the nozzle portion 48 of package 120, and the nozzle portion 148 of dropper cap 144. The nozzle cap would be provided only for storage and distribution purposes and then removed immediately before use of the package 20 or 120. If desired, the cap could be replaced over the nozzle to protect the contents of main container 22 or 122 during the period of non-use of a respective package for inoculation purposes.

We claim:

1. An in situ reconstitutable biological ampoule package comprising:

a container having a non-frangible, finger pressure deformable side wall of a synthetic resin material and provided with a closed end and an opening at the opposite end thereof;

a quantity of a reconstitutable biological composition within the container;

an ampoule within the container comprising a synthetic resin body provided with a side wall and an end wall portion integral with said side wall of the ampoule, said ampoule being adapted to store a quantity of a liquid medium for reconstituting the biological composition, the extremity of the ampoule side wall remote from said end wall portion being crimped with opposed, interengaging surfaces thereof bonded together to present an integral, V-shaped end closure for the ampoule, said ampoule further being provided with aperture means in the side wall thereof at said crimped portion of the side wall of the ampoule which is normally closed by an opposed side wall portion of the body and located in disposition such that when sufficient finger applied pressure is applied to the side wall of the container to force such side wall inwardly and thus effect deformation of the ampoule side wall, liquid medium is forced toward the end closure to an extent that the side wall portion of the ampoule blocking said aperture means is displaced thereby permitting release of the reconstituting medium from the ampoule through said aperture means to effect reconstitution of the biological composition; and a dropper cap over said opening of the container in closing relationship thereto thus permitting individual drops of the reconstituted biological composition to be selectively delivered from the package.

2. A biological package as set forth in claim 1 wherein the side wall of said container is formed of a synthetic resin material.

3. A biological package as set forth in claim 1 wherein said aperture means in the side wall of the ampoule is located in generally proximal relationship to the crimped and bonded side wall portion of the ampoule.

4. A biological package as set forth in claim 1 wherein the quantity of said reconstitutable biological composition is located adjacent the closed end of the container, and the extremity of the ampoule having said aperture means therein is proximal to the biological composition.

5. A biological package as set forth in claim 1 wherein said dropper cap comprises a cylindrical main body telescoped over the end of the container having said opening therein, and a nozzle portion provided with an elongated passage extending therethrough that communicates with the interior of the container.

6. A biological package as set forth in claim 1 wherein said container is of generally cylindrical configuration, and a cylindrical, deformable, non-frangible, synthetic resin protective cover member is telescoped over the container in enveloping relationship to a substantial part of the length of the ampoule.

7. An in situ reconstitutable biological ampoule package comprising:

a container having a non-frangible, finger pressure deformable side wall of synthetic resin material and provided with a closed end and an opening at the opposite end thereof;

a quantity of a reconstitutable live bacteria biological composition within the container;

an ampoule within the container comprising a finger pressure deformable synthetic resin body provided with a side wall and an end wall portion integral with said side wall of the ampoule, said ampoule being adapted to store a quantity of a liquid medium for reconstituting the biological composition, the extremity of the ampoule side wall remote from said end wall portion being crimped with opposed, interengaging surfaces thereof bonded together to present an integral, V-shaped end closure for the ampoule, said ampoule further being provided with normally closed aperture means in the side wall thereof at said crimped portion of the side wall of the ampoule, said aperture means having been closed at the time of bonding of said interengaging surfaces of said end extremity of the ampoule, said aperture means being located in said crimped portion in disposition such that when sufficient finger applied pressure is applied to the side wall of the container to force such side wall inwardly and thus effect deformation of the ampoule side wall, liquid medium is forced toward the end closure thereby opening the aperture means to release the reconstituting medium from the ampoule through said aperture means to effect reconstitution of the biological composition; and a dropper cap over said opening of the container in closing relationship thereto thus permitting individual drops of the reconstituted biological composition to be selectively delivered from the package.

* * * * *